United States Patent [19]
Pattison

[11] 3,949,112

[45] Apr. 6, 1976

[54] TREATMENT OF FIBROUS MATERIALS WITH POLYMERS AND COPOLYMERS OF FLUOROMETHYLATED DIENES

[75] Inventor: Victor A. Pattison, Clarence Center, N.Y.

[73] Assignee: Hooker Chemicals & Plastics Corporation, Niagara Falls, N.Y.

[22] Filed: Nov. 19, 1973

[21] Appl. No.: 416,917

Related U.S. Application Data

[63] Continuation-in-part of Ser. No. 788,009, Dec. 30, 1968, abandoned.

[52] U.S. Cl. ............... 428/262; 8/184; 260/85.5 R; 260/85.5 XA; 260/87.5 A; 260/87.5 B; 260/92.1 R; 260/346.1 R; 260/634; 260/653.3; 427/390; 427/391; 428/264; 428/274; 428/507; 428/512

[51] Int. Cl.² D21H 1/40; C07C 21/18; C07C 21/20; C07C 21/22

[58] Field of Search ............ 117/138.8 UF, 155 UA; 260/85.5 R, 85.5 X, 87.5 A, 87.5 B, 92.1 R, 346.1 R, 653.3, 634; 427/390, 391; 428/262, 264, 274, 507, 512; 8/184

[56] References Cited
UNITED STATES PATENTS

| | | | |
|---|---|---|---|
| 2,996,487 | 8/1961 | Bolstad et al. | 260/653.3 X |
| 3,078,245 | 2/1963 | Heine | 117/155 X |
| 3,081,274 | 3/1963 | Heine | 117/155 X |
| 3,116,269 | 12/1963 | Honn | 260/653.3 X |
| 3,282,905 | 11/1966 | Fasick et al. | 117/155 X |
| 3,518,114 | 6/1970 | Pittman et al. | 117/138.8 X |
| 3,637,614 | 1/1972 | Greenwood | 117/138.8 X |
| 3,654,244 | 4/1972 | Pittman et al. | 117/138.8 X |
| 3,754,057 | 8/1973 | Pacini et al. | 117/138.8 X |

*Primary Examiner*—Michael R. Lusignan
*Attorney, Agent, or Firm*—Peter F. Casella; John M. Petruncio

[57] ABSTRACT

Fibrous materials such as textiles and paper are rendered oil and water resistant by treatment with polymers and copolymers of

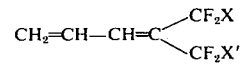

wherein X and X' are halogen.

12 Claims, No Drawings

TREATMENT OF FIBROUS MATERIALS WITH POLYMERS AND COPOLYMERS OF FLUOROMETHYLATED DIENES

This is a continuation-in-part application of Ser. No. 788,009, filed Dec. 30, 1968 now abandoned.

This invention relates to the treatment of fibrous materials. More particularly, this invention relates to the treatment of fibrous materials such as textiles and paper, with polymers and copolymers of fluoromethylated dienes, to confer water and oil repellancy properties thereto.

In accordance with the present invention, fibrous materials are treated with homopolymers and copolymers of fluoromethylated dienes of the formula

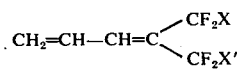

wherein X and X' are halogen, either alone in a homopolymerization reaction, or in the presence of at least one other dissimilar monomer copolymerizable therewith.

The fluoromethylated diene monomer may be readily prepared by reacting a fluoroacetone of the formula

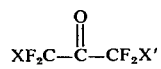

wherein X and X' are as previously defined, with propylene, in the presence of a Friedels-Craft catalyst, to yield an intermediate fluoromethylated alkenol of the formula

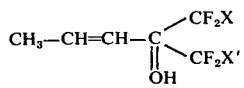

wherein X and X' are as previously defined. The resulting alkenol is then dehydrated to yield the monomeric butadiene. Depending upon whether or not it is desired to isolate the intermediary alkenols, the two steps may be combined and the dehydration agent optionally added to the olefin-fluoroacetone adduct reaction mixture without purification of the alkenols.

The fluoroacetone olefin adduct is prepared by combining fluoroacetone and the appropriate olefin in a molar ratio of up to 100 mole excess of either reactant, although a ratio of from 1:1 to 1:2 is preferred. Optionally, a solvent may be utilized; convenient solvents for the reaction include hexane or pentane, or other appropriate solvents inert to the conditions of the reaction. The reaction is carried out in the presence of a conventional Friedel-Crafts catalyst and at a temperature within the range of from about −100° to about 50°C., preferably from about −50° to 0°C.

Aluminum trichloride is an effective catalyst. Other suitable Friedel-Crafts type catalysts include boron trifluoride, tin chloride, zinc chloride, antimony fluoride and other aluminum halides.

The intermediate fluoromethylated alkenols are conveniently isolated from the reaction mixture by fractional distillation.

The reaction of fluoroacetones with the propylene evidently occurs with an alkyl rearrangement to form, as previously stated

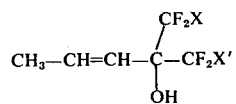

The adductive step provides a product comprised primarily of the stable trans isomer of the 2-alkenol, with the relatively unstable cis isomer present in only trace amounts. The isomers may be separated, if desired, by suitable gas chromatography procedures.

If isolation of the intermediate fluoromethylated alkenol is not desired, the dehydration agent may be added directly to the reaction mixture containing the fluoroacetone-olefin adduct.

To obtain the dehydration product, the dehydration agent is added after the adductive step of the reaction is complete and the reaction mixture has been heated to from about 20° to 300°C, preferably from about 50° to 150°C. Suitable dehydration agents include phosphorus pentoxide and concentrated sulfuric acid. While the dehydration agent may be added in proportions ranging from about 0.2 to 1000 moles per mole of fluoromethylated alkenol, the reaction is most efficiently carried out with an excess of the dehydration agent from about 10 to about 30 moles per mole of alkenol.

The polymerizable dehydration product is predominantly 1, 1-bis(halodifluoromethyl)-1, 3-butadiene, although minor amounts of 1, 1-bis(halodifluoromethyl)-tetrahydrofuran may be present. The conditions are controlled so that polymerization of the product is not induced prematurely.

The fluoromethylated butadiene may be polymerized or copolymerized with one or more monomers copolymerized therewith by conventional methods. The polymers and copolymers are useful as coating compositions, and are particularly valuable for their ability to confer water and oil repellancy to fibrous materials coated therewith.

The homopolymers of the fluoromethylated butadiene are characterized by the repeating units

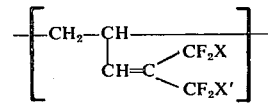

in the skeletal chain, wherein X and X' are as previously defined.

Homopolymerization of the fluoromethylated butadiene may be effected by polymerization methods known in the art, for example, by emulsion, solution, bulk or suspension techniques with free radical generators such as benzoyl peroxide, alkali metal persulfates or the liker preferably used to initiate the polymerization reaction.

The polymerization of 1,1-bis(halodifluoromethyl)-1,3-butadiene is conducted as to produce homopolymers having molecular weights on the order of from about 1000 to about 1,000,000, preferably on the order of from about 20,000 to about 200,000. Particularly desirable for use as fibrous material treating agents are those polymers having a molecular weight of about 50,000.

The monomers may be copolymerized with vinyl monomers such as styrene, acrylamide, acrylonitrile, ethyl acrylate, isoprene, haloprene, methylstyrene, vinyl pyrrolidone, vinyl halides, methyl methacrylate and methacryl halides. Particularly, efficacious as oil and water proofing agents are the styrene-fluoromethylated butadiene copolymer and the acrylamide-fluoromethylated butadiene copolymers.

The halomethylated butadiene monomer and copolymerizable monomer or monomers are polymerized in molar ratios of from about 1:100 to about 100:1, preferably from about 1:5 to about 5:1, to yield copolymers having molecular weights on the order of from about 1000 to about 1,000,000, preferably from about 20,000 to about 200,000.

Such molecular weights as are realized may be obtained by conducting the polymerization at temperatures on the order of from about 0°C to about 100°C for periods of from about 1 hour to about 24 hours.

The fibrous materials may be treated with the polymeric treating material by any suitable means known to the art, such as, for example, immersion or spraying techniques.

The examples which follow are provided to more clearly illustrate the nature of the present invention. All parts and percentages are by weight, and all temperatures are in degrees centigrade, unless otherwise specified.

EXAMPLE 1

Preparation of Propylene - Hexafluoro Actone Adducts

A mixture of 166 parts of fluoroacetone, 84 parts of propylene and 2 parts aluminum chloride in 1630 parts of pentane was allowed to warm slowly from −30°. At about −15° there was a gentle exotherm after which the reaction was stirred for 1 hour at ambient temperatures, then washed with 5 percent hydrochloric acid, dried over sodium sulfate and distilled (18 inch Vigreaux) to yield 150 parts (72 percent) of product boiling at 97°–100°. The composition of this product is 60 percent trans-1, 1-bis(trifluoromethyl)-2-buten-1-ol, 3 percent cis-1, 1-bis(trifluoromethyl)-2-buten-ol and 37 percent 1, 1-bis(trifluoromethyl)-3-buten-1-ol. Elemental analyses, infrared and nuclear magnetic resonance spectra confirmed the identity of the products.

EXAMPLE 2

Preparation of Propylene - Chloropentafluoroacetone Adducts

The process of Example 1 was repeated using 182 parts of chloropentafluoroacetone and 84 parts propylene yielding 82 percent (184 parts) of product boiling at 120°–130°. A mixture of isomers corresponding to that obtained in Example 1 was obtained. Elemental analyses, infrared and nuclear magnetic resonance spectra confirmed the identity of the product.

EXAMPLE 3

Preparation of Fluoromethylated Diene

A mixture of alkenols (272 parts) prepared in Example 1 from propylene and hexafluoroacetone and 740 parts of concentrated sulfuric acid were placed in a distillation flask fitted with a magnetic stirrer and an 8 inch Vigreaux column. The temperature of the reaction mixture was slowly raised until clear liquid started to distill at about 100°. The temperature was held at 100°–110° while 150 parts (59 percent) of essentially pure 1, 1-bis(trifluoromethyl)-1,3-butadiene distilled at 75°. Elemental analyses, infrared and nuclear magnetic resonance spectra confirmed the identity of the product.

EXAMPLE 4

Preparation of 1-Chloro-1, 1-Difluoro-2-Trifluoromethyl-2, 4-Pentadiene

The process of Example 3 was repeated using 22.4 parts of the propylene-chloropentafluoroacetone adduct prepared in Example 2 which was distilled slowly from 90 grams of concentrated sulfuric acid at 50 mm pressure. The distillate (12 parts) was dissolved in ether, washed with 5 percent sodium hydroxide solution, then washed with water and dried over sodium sulfate. Distillation (8 inch Vigreaux) effected 1-chloro-1, 1-difluoro-2-trifluoromethyl-2, 4-pentadiene boiling at 101°–102°. Elemental analyses, infrared and nuclear magnetic resonance confirmed the identity of the product.

EXAMPLE 5

Bulk Polymerization of 1, 1-bis-(Trifluoromethyl)-1, 3-Butadiene

A mixture of 1.90 parts of 1, 1-bis(trifluoromethyl)-1, 3-butadiene and 0.010 parts of benzoyl peroxide was placed in a vessel, flushed with nitrogen and heated at 60° for 66 hours. The reaction mixture was stripped of monomer by heating at 110°/1 mm for 1 hour. The polymeric residue obtained in essentially quantitive) yield had a molecular weight of 4500. Infrared spectra confirmed the identity of the product.

EXAMPLE 6

Emulsion Polymerization of 1, 1-bis-(Trifluoromethyl)-1, 3-Butadiene

A mixture of 11.8 parts of 1,1-bis-(trifluoromethyl)-1, 3-butadiene, 34 parts of water, 0.060 parts of potassium persulfate and 0.36 parts of sodium lauryl sulfate was placed in a vial, flushed with nitrogen and heated with vigorous stirring at 50°–60° for 20 hours. Evaporation of the water from the resultant emulsion gave a clear, tough polymer in essentially quantitive yield, having a molecular weight of 83,000. A clear, water-white, tough film was cast from its acetone solution. The infrared spectrum is similar to that from the bulk polymerization.

EXAMPLE 7

Preparation of Copolymer of 1, 1-bis-(Trifluoromethyl)-1, 3-Butadiene and Acrylamide The emulsion polymerization process of Example 6 was repeated using equimolar quantities of 1, 1-bis-(trifluoromethyl)-1, 3-butadiene and acrylamide. A high molecular weight 1:1 copolymer of 1, 1-bis(trifluoromethyl)-1, 3-butadiene and acrylamide was obtained.

EXAMPLE 8

Preparation of Methylolated Copolymer of 1, 1-bis(Trifluoromethyl)-1, 3-Butadiene and Acrylamide A mixture of 316 parts of acrylamide, 9.8 parts of 1, 1-bis(trifluoromethyl)-1, 3-butadiene, 24 parts of water, 0.06 parts of potassium persulfate, and 0.36 parts of sodium lauryl sulfate were heated and stirred at 50°–60° for 20 hours to form a viscous emulsion. This emulsion was diluted with 50 parts of water and brought to pH 8.0 with sodium carbonate. At this point 8.5 parts of 37 percent formaldehyde was added, and the emulsion was stirred overnight at ambient temperatures to produce a resin which is methylolated 1:1 copolymer of 1, 1-bis-(trifluoromethyl)-1,3-butadiene and acrylamide.

EXAMPLE 9

Preparation of Copolymer of 1, 1-bis(Trifluoromethyl)-1,3-Butadiene and Acrylonitrile The emulsion polymerization process of Example 6 was repeated using equimolar quantities of 1, 1-bis(trifluoromethyl)-1, 3-butadiene and acrylonitrile. A high molecular weight 1:1 and copolymer of 1, 1-bis(trifluoromethyl)-1, 3-butadiene and acrylonitrile was obtained. A clear, water-white, tough film was cast from its acetone solution. Infrared spectra confirmed the structure of the polymer.

EXAMPLE 10

Preparation of Copolymers of 1, 1-bis(Trifluoromethyl)-1,3-Butadiene and Styrene The emulsion polymerization of Example 6 was repeated using equimolar quantities of 1,1-bis(trifluoromethyl)1, 3-butadiene and styrene. A high molecular weight (163,000) 1:1 copolymer of 1, 1-bis(trifluoromethyl)-1,3-butadiene and styrene was obtained. A clear water-white tough film was cast from its acetone solution. Infrared spectra confirmed the structure of the polymer.

EXAMPLE 11

Preparation of Copolymer of 1, 1-bis(Trifluoromethyl)-1, 3-Butadiene and Ethyl Acrylate The emulsion polymerization process of Example 6 was repeated using equimolar quantities of 1, 1-bis(trifluoromethyl)-1,3-butadiene and ethyl acrylate. A high molecular weight (110,000) 1:1 copolymer of 1, 1-bis(-trifluoromethyl)-1,3-butadiene and ethyl acrylate was obtained. A slightly opaque, nearly water-white film was cast from its acetone solution. Infrared spectra confirmed the structure of the polymer.

EXAMPLE 12

Preparation of Copolymer of 1, 1-bis(Trifluoromethyl)-1, 3-Butadiene and Isoprene The emulsion polymerization of Example 6 was repeated using equimolar quantities of 1, 1-bis(trifluoromethyl)-1,3-butadiene and isoprene. A high molecular weight (173,000) 1:1 copolymer of 1, 1-bis(trifluoromethyl)-1,3-butadiene and isoprene was obtained. A slightly opaque, elastomeric film was cast from its acetone solution. Infrared spectra confirmed the structure of the polymer.

EXAMPLE 13

Treatment of Textiles with Methylolated Copolymer of Acrylamide and 1, 1-bis(Trifluoromethyl)-1, 3-Butadiene The product of Example 8 was applied to cotton broadcloth at 1, 2 and 5 percent levels in the padding solution, and the treated cloth was subsequently cured at 160° in the presence of a zinc nitrate catalyst. This treated cloth was then subjected to water and grease resistance tests. The oil rating test was run as described in the book *Chlorine Chemistry*, J. H. Simons, vol, V, (1964), Academic Press, pp. 402–404. The methanol-water test is a correlation of the oil rating test using water instead of mineral oil, methanol instead of n-heptane, and using a rating system of 0–100, where 0 is poor or failure and 100 is excellent. The spray rating test refers to Test Method 22-1961 of the American Association of Textile Chemists and Colorists.

A control sample of cotton broadcloth, not treated, with the resin of Example 8, had a methanol-water rating of less than zero, an oil rating of less than 50 and a spray rating of zero. A sample treated with a 1 percent resin padding solution exhibited a methanol-water rating of 30–40, an oil rating of 50 and a spray rating of 70–80. A sample treated with a 2 percent resin padding solution exhibited a methanol-water rating of 50–60, an oil rating of 50 and a spray rating of 100. A similar sample tested with a 5 percent padding solution exhibited a methanol-water rating of 50–60, an oil rating of 70 and a spray rating of 100. After 5 home washes, the three samples exhibited respectively methanol-water ratings of 0, 30, and 40; oil ratings of 50, 50 and 50; spray ratings of 0, 50–70 and 100.

EXAMPLE 14

Treatment of Paper with Homopolymer of 1, 1-bis(Trifluoromethyl)-1,3-Butadiene

The process of Example 13 was repeated using the emulsion polymer of Example 6 as the treating agent, wherein 50 lb. Kraft paper was treated and subsequently cured at 130°/15 minutes. An untreated control exhibited a methanol-water rating of zero and an oil rating of 50. Treated samples treated with solutions of 0.05, 0.1 and 0.5 and 2.5 percent resin levels exhibited a methanol-water rating, respectively, of 50, 80, 80 and 80 and an oil rating, respectively, of 60, 80, 80 and 80.

EXAMPLE 15

Treatment of Paper with 1:1 Copolymer of 1, 1-bis(Trifluoromethyl)-1, 3-Butadiene and Acrylonitrile The process of Example 14 was repeated using the copolymer of Example 9. The treated paper exhibited methanol-water ratings, respectively, of 10, 50, 60 and 70 and oil ratings, respectively, of 50, 60, 80 and 80.

EXAMPLE 16

Treatment of Paper with 1:1 Copolymer of 1, 1-bis(Trifluoromethyl)-1, 3-Butadiene and Ethyl Acrylate The process of Example 14 was repeated using the copolymer of Example 11. The treated paper exhibited methanol-water ratings, respectively, of 0, 20, 60 and 80 and oil ratings, respectively, of 50, 60, 80 and 80.

It is to be understood that the details provided in the foregoing specification can be modified by those skilled in the art without departing from the scope of the invention.

What is claimed is:

1. A method for rendering fibrous materials water and oil resistant which comprises contacting said fibrous material with a polymer or copolymer of 1,1-bis(halodifluoromethyl)-1,3-butadiene characterized by the repeating units

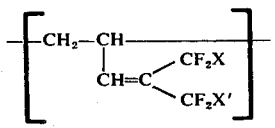

in the skeletal chain wherein said copolymer contains said repeating units in a molar ratio of from about 1:100 to about 100:1 of a copolymerizable monomer, to deposit a water and oil resistant amount of polymer or copolymer thereon, and thereafter drying the thus-treated fibrous material.

2. A method as defined by claim 1 wherein the 1,1-bis(halodifluoromethyl)-1,3-butadiene is 1,1-bis(trifluoromethyl)-1,3-butadiene.

3. The method as defined by claim 1 wherein the polymer is a 1:1 copolymer of 1,1-bis(trifluoromethyl)-1,3-butadiene and acrylonitrile.

4. The method of defined by claim 1 wherein the polymer is a 1:1 copolymer of 1,1-bis(trifluoromethyl)-1,3-butadiene and acrylamide.

5. The method as defined by claim 1 wherein the polymer is a methylolated 1:1 copolymer of 1,1-bis(trifluoromethyl)-1,3-butadiene and acrylamide.

6. The method as defined by claim 1 wherein the polymer is a 1:1 copolymer of 1,1-bis(trifluoromethyl)-1,3-butadiene and styrene.

7. The method as defined by claim 1 wherein the polymer is a 1:1 copolymer of 1,1-bis(trifluoromethyl)-1,3-butadiene and ethyl acrylate.

8. The method as defined by claim 1 wherein the polymer is a 1:1 copolymer of 1,1-bis(trifluoromethyl)-1,3-butadiene and isoprene.

9. The method as defined by claim 1 wherein said fibrous material is textile material.

10. The method as defined by claim 1 wherein said fibrous material is paper.

11. Textile materials treated in accordance with the method of claim 9.

12. Paper treated in accordance with the method of claim 10.

* * * * *